United States Patent [19]
Sabahi

[11] Patent Number: 5,840,996
[45] Date of Patent: Nov. 24, 1998

[54] PRODUCTION OF BROMINATED METHOXYNAPHTHALENE COMPOUNDS

[75] Inventor: Mahmood Sabahi, Baton Rouge, La.

[73] Assignee: Albemarle Corporation, Richmond, Va.

[21] Appl. No.: 854,131

[22] Filed: May 8, 1997

[51] Int. Cl.⁶ ................................................. C07C 41/22
[52] U.S. Cl. .......................................................... 568/634
[58] Field of Search ............................................ 568/634

[56] References Cited

U.S. PATENT DOCUMENTS

| | | | |
|---|---|---|---|
| 4,628,123 | 12/1986 | Borsotti | 568/634 |
| 5,243,088 | 9/1993 | Jacquot et al. | 568/656 |
| 5,256,829 | 10/1993 | Jacquot | 568/737 |
| 5,412,150 | 5/1995 | Wessel | 560/56 |
| 5,426,243 | 6/1995 | Lecouve | 568/737 |

FOREIGN PATENT DOCUMENTS 380563 9/1932 United Kingdom.

OTHER PUBLICATIONS

Bray, et al., "The Catalytic Decomposition of Hydrogen Peroxide in a Bromine–Bromide Solution, and a Study of the Steady State", J. of Am. Chem. Soc., 1923, v. 45, pp. 1251–1280.

Choudary, et al., "Regioselective Oxybromination of Activated Aromatic Compounds Catalyzed by Ammonium Molybdate", Synlett, 1994, pp. 450.

Kajigaeshi, et al., "Halogenation Using Quaternary Ammonium Polyhalides, IV, Selective Bromination of Phenols by Use of Tetraalkylammonium Tribromides", Bull. Chem. Soc. Jpn. 1987, v. 60, pp. 4187–4189.

Kornblum, et al., "Solvation as a Factor in the Alkylation of Ambident Anions: The Importance of the Hydrogen Bonding Capacity of the Solvent", J. Am. Chem. Soc., 1963, v. 85, pp. 1141–1147.

March, Advanced Organic Chemistry, Reactions, Mechanisms, and Structure, 3rd Ed., Wiley–Interscience Publication, pp. 322–325, 1985.

Marques, et al., "Facile Hydrodehalogenation with $H_2$ and Pd/C Catalyst under Multiphase Conditions. . . .", J. Org. Chem., 1995, v. 60, pp. 2430–2435.

Pinder, "The Hydrogenolysis of Organic Halides", Synthesis, 1980, pp. 425–452.

Rajagopal, et al., "Mechanism of Palladium–Catalyzed Transfer Hydrogenolysis of Aryl Chlorides by Formate Salts", J. Org. Chem., 1995, vol. 60, pp. 1347–1355.

*Primary Examiner*—Gary Geist
*Assistant Examiner*—Sreeni Padmanabhan
*Attorney, Agent, or Firm*—E E. Spielman, Jr.

[57] ABSTRACT

Bromine is generated in situ in a mixture formed by mixing together 2-methoxynaphthalene, hydrogen bromide, at least one peroxidic compound and a chemically indifferent organic liquid solvent or diluent under conditions effective to produce 1,6-dibromo-2-methoxynaphthalene. Optionally, but preferably, water is also included in the mixture. Regioselective hydrodebromination of 1,6-dibromo-2-methoxynaphthalene with hydrogen and tungsten carbide enables production of 2-bromo-6-methoxynaphthalene.

22 Claims, No Drawings

PRODUCTION OF BROMINATED METHOXYNAPHTHALENE COMPOUNDS

TECHNICAL FIELD

This invention relates to efficient process for the synthesis of 1,6-dibromo-2-methoxynaphthalene. This invention also relates to an efficient process for the synthesis of 2-bromo-6-methoxynaphthalene.

BACKGROUND

2-Bromo-6-methoxynaphthalene is a useful starting material for use in the synthesis of pharmaceutically active agents such as naproxen and nabumetone. 2-Bromo-6-methoxynaphthalene is usually formed by bromination of 2-naphthol with elemental bromine (which produces 1,6-dibromo-2-naphthol as the principal product), hydrodebromination of the 1,6-dibromo-2-naphthol to form 6-bromo-2-naphthol, and methylation of the 6-bromo-2-naphthol with a reagent such as methyl sulfate or methanol. See in this regard U.S. Pat. No. 5,256,829.

While this process sequence is suitable for large scale production of 2-bromo-6-methoxynaphthalene, it does possess some practical limitations, such as costs associated with disposal of co-products, problems resulting from development of coloration during synthesis operations, and plant throughput inefficiencies.

SUMMARY OF THE INVENTION

In one of its embodiments this invention provides a new, highly efficient process for the production of 1,6-dibromo-2-methoxynaphthalene from 2-methoxynaphthalene. Another embodiment of this invention is anew, efficient process wherein 1,6-dibromo-2-methoxynaphthalene is produced and regioselectively hydrodebrominated to form 2-bromo-6-methoxynaphthalene. The novel process technology of this invention is deemed to avoid at least some of the limitations associated with the production of 2-bromo-6-methoxynaphthalene by the above prior art process.

The production of 1,6-dibromo-2-methoxynaphthalene from 2-methoxynaphthalene pursuant to this invention is effected by generating the bromine in situ by use of hydrogen bromide and a suitable peroxidic compound, preferably hydrogen peroxide. For convenience, this process is sometimes referred hereinafter as "the bromination reaction". In one embodiment, all of the bromine used in the bromination reaction is generated in situ. In another embodiment, about one equivalent of elemental bromine is used to form monobrominated 2-methoxynaphthalene and the hydrogen bromide liberated in the monobromination is then converted into bromine (preferably in situ by addition of a suitable peroxidic compound) whereby the 1,6-dibromo-2-methoxynaphthalene is formed. In this embodiment, substantially all of the bromine is utilized effectively in the process.

The regioselective hydrodebromination of 1,6-dibromo-2-methoxynaphthalene to form 2-bromo-6-methoxynaphthalene can be conducted in any of several different ways, but preferably is performed by reacting 1,6-dibromo-2-methoxynaphthalene with hydrogen or a precursor compound that generates nascent hydrogen in the medium of the reaction, in a halogen-containing liquid solvent or diluent comprising at least about 50% by weight of (a) at least one liquid organic halide solvent in which the halogen content has an atomic number of 35 or less or (b) a mixture of water and at least one such liquid organic halide solvent or diluent, and in the presence of catalytically effective amounts of (i) a tungsten carbide-based catalyst, and (ii) at least one phase transfer catalyst, such that 2-bromo-6-methoxynaphthalene is formed. For convenience, this process, however performed, is sometimes referred hereinafter as "the hydrodebromination reaction".

Other embodiments and features of this invention will become still further apparent from the ensuing description and appended claims.

FURTHER DETAILED DESCRIPTION

The Bromination Reaction

The bromination reaction is typically conducted in the liquid phase using a halocarbon or halohydrocarbon as liquid reaction solvent or diluent. The halogen content of such solvents is one or more fluorine, chlorine and/or bromine atoms (i.e., halogen of atomic number 35 or less). Examples of such solvents include hexafluorobenzene, octafluorotoluene, perfluorodecalin, carbon tetrachloride, chloroform, ethylene dibromide, 1,1-dibromoethane, bromobenzene, chlorobenzene, fluorobenzene, 1-bromo-3-chlorobenzene, 1-chloro-4-fluorobenzene, o-bromotoluene, m-bromotoluene, o-chlorotoluene, m-chlorotoluene, p-chlorotoluene, o-fluorotoluene, m-fluorotoluene, p-fluorotoluene, α-chloro-α,α-difluorotoluene, 1,1,1,2-tetrachloro-2,2-difluoroethane, 1,1,2,2-tetrachloro- 1,2-difluoroethane, 1,1,2-tribromoethane, bromocyclohexane, chlorocyclohexane, trichloroethylene, perchloroethylene, and like compounds. Polychloroalkanes are preferred, and include such materials as ethylene dichloride (1,2-dichloroethane), 1,1-dichloropropane, 1,2-dichloropropane, 1,3-dichloropropane, 1,1,1-trichloroethane, 1,1,2-trichloroethane, 1,1,2,2-tetrachloroethane, and dichloromethane. Of these, ethylene dichloride is most preferred.

Other solvents or diluents which can be used in the bromination reaction include alcohols, organic acids, water, hydrocarbons, inorganic acids, glycols, and the like.

Preferably, the reaction medium also contains water in an amount of up to about 50% by weight of the solvent medium (i.e., excluding the reactants).

Organic peroxides, hydroperoxides, peroxycarbonates and persulfates can be used as peroxidic compounds for the bromination reaction (e.g., tert-butylhydroperoxide, n-butyl hydroperoxide, tert-butylperoxide, peroxyacetic acid, lauroyl peroxide, cumene hydroperoxide, etc.). However the most preferred peroxidic compound is hydrogen peroxide, preferably employed as an aqueous solution (3% or more $H_2O_2$, and preferably 25% or more $H_2O_2$), and most preferably 30% aqueous hydrogen peroxide is used.

Aqueous hydrogen bromide is preferably used in the bromination reaction, but gaseous hydrogen bromide can be charged into the reaction mixture, especially where the reaction medium contains water.

The proportions of hydrogen bromide and peroxidic compounds relative to each other can be varied within rather wide limits. Typically, however, the proportions used will fall in the range of about 1 to about 1.1 moles of peroxidic compound per mole of hydrogen bromide. The proportions of hydrogen bromide relative to the 2-methoxynaphthalene typically fall in the range of about 4.5 to about 1 moles of hydrogen bromide per mole of 2-methoxynaphthalene.

Heat is evolved when conducting the bromination reaction of this invention. Thus it is desirable to utilize controlled continuous or intermittent portionwise addition of the peroxidic compound to a suitably agitated mixture formed from the 2-methoxynaphthalene, the solvent, and the hydrogen bromide. Temperatures for the bromination reaction are usually maintained in the range of about 20° to about 90° C. and preferably, the reaction is performed at one or more temperatures in the range of about 50° to about 70° C. By suitably controlling the rate of addition of the peroxidic compound to the foregoing mixture, it is possible to conduct the reaction at temperatures within this range without need for applying any external heat. The reaction period is usually in the range of about 0.5 to about 4 hours.

It will be recalled that one of the embodiments of this invention comprises forming 1,6-dibromo-2-methoxynaphthalene in a two-stage bromination wherein elemental bromine is used in the first stage to form monobrominated 2-methoxynaphthalene, and in the second stage the hydrogen bromide formed in the first stage reaction is converted, preferably in situ, into bromine by addition of a suitable peroxidic compound. In the first stage of this embodiment, approximately one equivalent of bromine is reacted with the 2-methoxynaphthalene at a temperature in the range of about 10° to about 60° C. This reaction is typically conducted in the liquid phase using a halocarbon or halohydrocarbon such as described above as liquid reaction solvent or diluent. Hydrogen bromide co-produced in the first stage is either dissolved in the solvent or diluent, or complexed by inclusion in the bromination reaction mixture of a suitable hydrogen bromide acceptor such as a tertiary amine. In the second stage reaction the hydrogen bromide co-product is converted in situ into bromine by use of a suitable peroxidic compound in the manner described above so that 1,6-dibromo-2-methoxynaphthalene is formed.

The Hydrodebromination Reaction

This process, when utilized, comprises reacting all or at least a portion of the 1,6-dibromo-2-methoxynaphthalene formed with hydrogen or a precursor compound that generates nascent hydrogen in the medium of the reaction such that regioselective removal of bromine occurs yielding 2-bromo-6-methoxynaphthalene and hydrogen bromide as the principal products.

The preferred processes for conducting the hydrodebromination reaction involve use of a tungsten carbide-based catalyst, most preferably together with a phase transfer catalyst. The process involving use of such tungsten carbide catalysts is described in U.S. Pat. No. 5,256,829 to R. Jacquot. The preferred process for conducting the hydrodebromination reaction involving the use of a tungsten carbide-phase transfer catalyst system will now be described.

This preferred process is performed in a halogen-containing liquid solvent comprising at least 50% by weight of (a) at least one organic halide solvent or (b) a mixture of water and at least one organic halide solvent, such as, for example, a polychloroalkane. In addition, the reaction is performed in the presence of catalytically effective amounts of (i) a tungsten carbide-based catalyst, and (ii) at least one phase transfer catalyst. It will be noted that this is a controlled or selective hydrodebromination reaction wherein one of two bromine atoms of the 1,6-dibromo-2-methoxynaphthalene is removed in preference to the other, and the one that remains is in the desired position (i.e., as 2-bromo-6-methoxynaphthalene). Thus the reaction is in fact a regiospecific or regioselective hydrodebromination reaction.

The liquid organic halides used as solvent media for the hydrodebromination reaction are liquids composed of carbon and halogen atoms, and in most cases hydrogen atoms as well. The halogen content of such solvents is one or more fluorine, chlorine and/or bromine atoms (i.e., halogen of atomic number 35 or less). Thus the solvent medium for the hydrodebromination reaction can be one or more perhalocarbons or one or more halohydrocarbons or a mixture of one or more perhalocarbons or one or more halohydrocarbons, in all cases where the halogen atom content has an atomic number of 35 or less. These solvents can have one or more halogen atoms in the molecule, and when two or more halogen atoms are present in the molecule, they can be the same or different halogen atoms (i.e., they can be fluorine and chlorine atoms, chlorine and bromine atoms, fluorine and bromine atoms, or fluorine, chlorine and bromine atoms). Preferred solvents for this reaction are the halogen-containing saturated aliphatic compounds, halogen-containing saturated cycloaliphatic compounds and halogen-containing aromatic compounds, and of these the chloroalkanes are preferred. Most preferred are polychloroalkanes, especially ethylene dichloride. These solvents may be used in combination with water as a mixed phase reaction medium. Preferably, however, the halocarbon or halohydrocarbon solvent is either anhydrous or it contains small amounts of water and in this latter case, the amount of water is preferably small enough such that the solvent remains visually clear and thus does not possess a visually readily-observable separate liquid phase. The conjoint use of tungsten carbide and phase transfer catalyst in conjunction with such reaction media afford both high selectivity and shortened reaction periods.

In general, halocarbons and halohydrocarbons referred to above in connection with the bromination reaction can be used in the hydrodebromination reaction.

When water is present in the organic halide solvent, it is desirable to avoid an amount of water that will deactivate the catalyst. Thus the amount of water used is usually less than 10% by weight of the total weight of water plus halocarbon and/or halohydrocarbon solvent. A particularly preferred reaction medium is a visually clear mixture composed of ethylene dichloride and water in which the amount of water is below or up to, but not in excess of, the saturation point when the mixture is at 25° to 30° C. The reaction medium should be essentially free of iron or other dissolved metals that would interfere with the reaction.

As noted above, the tungsten carbide catalysts used in the hydrodebromination reaction are catalysts based on tungsten carbide, and suitable catalysts of this type are described in detail in U.S. Pat. No. 5,256,829.

Most preferably, the tungsten carbide catalyst used in the reaction is in the form of essentially pure tungsten carbide itself in a very fine powdery state, e.g., with an average particle size of about 0.9 micron and containing particles as small as 0.1 micron.

Amounts of tungsten carbide-based catalyst are typically in the range of about 5 to about 50 wt % of WC based on the weight of 1,6-dibromo-2-methoxynaphthalene initially present in the reaction mixture. Preferred amounts of the above preferred finely-divided tungsten carbide are in the range of about 10 to about 30 wt % of WC based on the weight of 1,6-dibromo-2-methoxynaphthalene initially present.

Various types of phase transfer catalysts such as crown ethers, crypt compounds, quaternary phosphonium complexes, and quaternary ammonium complexes can be used as the co-catalyst. Of these, the quaternary ammonium complexes are most preferred.

Suitable quaternary ammonium complexes include compounds depicted by the formula:

where $R^1$, $R^2$, $R^3$, and $R^4$ are, independently, hydrocarbyl groups (e.g., alkyl, cycloalkyl, aryl, aralkyl, alkenyl, alkoxylated alkylene polyamine groups, alkoxylated hydroxyhydrocarbyl groups, and/or heterocyclic groups in which the heteroatom or atoms are nitrogen atoms), and X is an anion such as a halide ion, a hydroxyl anion, a monoalkylsulfate anion, a sulfonate anion, a hydrogen sulfate anion, or the like. Examples of such compounds include:

tetrabutylammonium bromide
tetrahexylammonium bromide
trimethyldodecylammonium chloride;
trimethyldodecylammonium bromide;
trimethyltetradecylammonium chloride;
trimethyltetradecylammonium bromide;
trimethylhexadecylammonium chloride;
trimethylhexadecylammonium bromide;
trimethyloctadecylammonium chloride;
trimethyloctadecylammonium bromide;
dimethylalkylbenzylammonium chloride; where the alkyl groups are one or more of the following: $n-C_{12}H_{25}$; $n-C_{14}H_{29}$; $n-C_{16}H_{33}$; $n-C_{18}H_{37}$;
methylbis(2-hydroxyethyl)octadecylammonium chloride;
methylpolyoxyethylene (15) octadecylammonium chloride;
n-dodecyl (61%), n-tetradecyl (23%) dimethylbenzylammonium chloride;
n-tetradecyl (60%), n-hexadecyl (30%) dimethylbenzylammonium chloride;
n-dodecyl (40%), n-tetradecyl (50%) dimethylbenzylammonium chloride;
n-dodecyl (61%), n-tetradecyl (23%) dimethylbenzylammonium chloride;
n-octadecyldimethylbenzylammonium chloride;
42% solution of mixed n-tetradecyl (40%) and n-hexadecyl (60%) dimethylbenzylammonium chlorides;
8% solution of dialkylmethylbenzylammonium chloride;
n-dodecyl (35%), tetradecyl (5%), hexadecyl (60%) dimethylbenzylammonium chloride;
n-dodecyl (20%), tetradecyl (50%), hexadecyl (30%) dimethylbenzylammonium bromide;
methyl sulfate quaternary of ethoxylated tallow diethylenetriamine condensate;
methyl sulfate quaternary of propoxylated tallow diethylenetriamine condensate; and
1-(tallow amidoethylene)-2-nor(tallow alkyl)-2-imidazolinium, methyl sulfate quaternary.

Methods of preparation for the quaternary ammonium compounds are known and reported in the literature. Typical reactions are, for example, reaction of a suitable tertiary amine with an alkylating agent, which can be an alkyl ester or alkyl halide. Such reactions are summarized in Kirk-Othmer, *Encyclopedia of Chemical Technology*, Third Edition, Volume 19.

The quaternary ammonium complex is used in a co-catalytically effective amount, typically in the range of about 0.01 to about 10 wt %, and preferably in the range of about 0.1 to about 1 wt %, of the 1,6-dibromo-2-methoxynaphthalene initially present.

Quaternary phosphonium complexes which may be employed include compounds depicted by the formula:

where $R^5$, $R^6$, $R^7$ and $R^8$ are, independently, substantially straight chain hydrocarbyl groups (e.g., alkyl, alkenyl, alkoxyalkyl, poly(alkoxy)alkyl, etc., groups which are either non-branched or if branched, have branching in remote positions that do not provide steric hindrance), and X is an anion such as a halide ion. Methods for the preparation of such complexes include reaction of phosphine with sterically unhindered alkyl halides. Examples of such compounds include: tetrabutylphosphonium bromide, hexadecytributylphosphonium chloride, methyltriphenylphosphonium iodide, 2-hydroxyethyltriphenylphosphonium bromide, tetrabutylphosphonium chloride, tetraphenylphosphonium chloride, tetraphenylphosphonium bromide, tetrabutylphosphonium iodide, methyltrioctylphosphonium bromide, and analogous compounds.

Co-catalytically effective amounts of quaternary phosphonium complex used will typically fall in the range of about 0.01 to about 10 wt %, and preferably in the range of about 0.1 to about 1 wt %, of the 1,6-dibromo-2-naphthalene initially present.

For descriptions of crown ethers such as 18-crown-6 and crypt compounds such as crypt-222 which may be used in the process, one may refer, for example to such references as U.S. Pat. No. 3,687,978; J. J. Christensen, et al., *Chem. Rev.*, 1974, 74, 351; J. S. Bradshaw, et al., *Heterocycl. Chem.*, 1974, 11, 649; C. J. Pedersen, et al., *Angew. Chem. Int. Ed. Engl.*, 1972, 11, 16; Technical Bulletin of PCR Incorporated entitled KRYPTOFIX; and *J. Org. Chem*, 1977, 42(10), 2A. The crown ether or crypt compound is used in a catalytically effective amount, which typically is in the range of about 0.01 to about 0.1 mole per mole of 1,6-dibromo-2-naphthalene initially present in the reaction mixture.

To initiate the hydrodebromination reaction, the reaction system should contain a small catalytically effective amount of an acidic substance, most preferably hydrogen bromide. This is typically an amount within the range of about 1 to about 10 wt % of the total weight of the reaction system that ensures that the reaction is initiated and proceeds at a satisfactory rate without at the same time resulting in the formation of appreciable quantities of 2-methoxynaphthalene through overhydrodebromination. The optimum amount in any case should be determined by performing a few pilot tests, as the amount appears to depend upon a number of factors which can vary from case to case.

It is not known exactly how (i.e., the mechanism by which) either catalyst component actually functions during the reaction nor the actual state or composition of the catalyst components when functioning in the reaction mixture. Therefore, as regards catalyst composition, the co-catalyst materials are identified herein as to their respective compositions prior to being combined with any other substance being used in the process. After addition to, and/or mixing with, one or more other components used in the process and/or during the course of the process itself, either or both co-catalysts may change in its respective composition, and if so, the resultant changed material—whatever its makeup and however many changes it may undergo—may be in whole or in part responsible for the functioning of the catalyst.

As indicated above, it is highly desirable, if not highly important, to ensure that the liquid phase of the hydrodebromination reaction contains an acidic catalyst most preferably hydrogen bromide during at least substantially the entire reaction period of such hydrodebromination reaction.

Accordingly, unless absolutely pure 1,6-dibromo-2-methoxynaphthalene is available for use as the starting material (in which case a small catalytically effective amount of an acidic catalyst, most preferably hydrogen bromide, is introduced into the reaction mixture), a small amount of hydrogen bromide should be present to ensure initiation of the reaction. From then on it is particularly preferred, and important when seeking the best results, to control the amount of hydrogen bromide by-product remaining in the liquid phase by purging the reaction mixture with hydrogen or an inert gas such as nitrogen, argon, neon, etc., so that most of the by-product hydrogen bromide is continuously removed as it is formed while still leaving a small catalytically effective amount of hydrogen bromide dissolved in the liquid reaction medium. The rate of purging is best determined in any given situation by running a few pilot experiments and determining by analysis of the product, the amount of "overhydrodebrominated" product that exists in the product. If too much hydrogen bromide is left in the product, the amount of non-brominated 2-methoxynaphthalene will become excessive. Conversely, if too little hydrogen bromide is left in the liquid phase, incomplete reactions with excessive amounts of brominated products will result. Thus preferably the rate of purge is controlled such that the recovered 2-bromo-6-methoxynaphthalene product on completion of the regioselective hydrodebromination contains no more than about 1 wt % (most preferably no more than about 0.5 wt %) of non-brominated 2-methoxynaphthalene, and no more than about 5 wt % (most preferably no more than about 1 wt %) of aryl-polybromo impurities.

The best way of performing the controlled purge of by-product hydrogen bromide from the reaction mixture is to sparge the reaction mixture with hydrogen throughout substantially the entire hydrodebromination reaction period. In this operation the hydrogen should be continuously introduced into the lowermost portion of the reaction mixture so that it sweeps through substantially the entire reaction mixture and the resultant vapors should be continuously removed from the headspace above the reaction mixture at a rate sufficient to keep the gaseous input to and output from the reaction in a substantially equilibrium condition. Thus reactors equipped with sparger inlets at their lower interiors and gaseous offtake outlets at their upper interiors are preferably employed. The gaseous mixture of hydrogen and entrained hydrogen bromide is preferably passed through a scrubber system containing water and/or a suitable base, e.g., aqueous sodium hydroxide, to remove the hydrogen bromide from the hydrogen so that the hydrogen can be recycled continuously in the purging operation.

The hydrodebromination reaction when conducted with purge of hydrogen bromide from the reaction mixture is typically conducted at temperatures in the range of about 50° to about 150° C. at pressures in the range of about 65 to about 200 psig, and preferably at temperatures in the range of about 90° to about 120° C. at pressures in the range of about 65 to about 120 psig.

If a purge of hydrogen bromide is not used, the hydrodebromination reaction should be performed at relatively high temperatures and pressures (e.g., 100° to 300° C. at 500 to 1500 psig).

The invention is illustrated by the following examples wherein percentages are by weight unless otherwise specified. These examples are not intended to limit, and should not be construed as limiting, the scope of this invention.

EXAMPLE 1

A 50-mL 3-necked flask (thermometer, magnetic stirrer, condenser, dropping funnel) was charged with 2-methoxynaphthalene (3.95 g, 25.0 mmol), ethylene dichloride (15 mL or 18.7 g), and 48% aqueous HBr (10.14 g, 60.0 mmol). To the stirred mixture at 25° C. (no external heating or cooling) was added 28% aqueous $H_2O_2$ (7.28 g, 60.0 mmol) dropwise. After 7 minutes, one-half (3.60 g, 30.0 mmol) of the peroxide had been added and the reaction temperature had increased to 64° C. The remaining peroxide was added dropwise over a 33-minute period at a rate to maintain the reaction temperature at 60°–63 ° C. After a total reaction time of 45 minutes, an internal standard (tetradecane) was added to an aliquot that was then worked up and analyzed by GC. The weight of the product was found to be 6.66 g (21.1 mmol) for an 84% yield of 1,6-dibromo-2-methoxynaphthalene.

Among the features of this invention are the exceptionally high conversions that can be achieved by its practice, as contrasted to the relatively poor conversions that are achieved when attempting to utilize the same in situ bromination procedure with closely related naphthalene derivatives, namely 2-naphthol and 1-bromo-2-naphthol. This feature was demonstrated by an extended series of comparative runs presented in Examples 2 and 3 and in Table 1. For completeness, Table 1 includes the run of Example 1 as well.

EXAMPLES 2–3

Comparative runs were conducted using the bromination procedure as in Example 1 with temperatures in the range of 50° to 60° C. The other conditions and the results of these runs are summarized in Table 1 in which the following designations are used:

EDC: ethylene dichloride
MeOH: methanol
2-MN: 2-methoxynaphthalene
2-N: 2-naphthol
1-BN: 1-bromo-2-naphthol
LAS: linear alkylbenzene sulfonate Examples A–N are comparative examples, not of this invention. Conversions are given in terms of monobromide to dibromide; the conversion of 2-N to the monobromide was always 100%.

TABLE 1

In Situ Bromination Reactions

| Ex. | Solvent (% $H_2O$) | Reactant | Mole Ratio* | Time (Hr) | Conversion (%, Normalized) |
|---|---|---|---|---|---|
| 1 | EDC (35) | 2-MN | 1.0:2.4:2.4 | 0.7 | 98 |
| 2 | EDC (21) | 2-MN | 1.0:2.8:2.8 | 1.8 | 100 |
| 3 | EDC (17) | 2-MN | 1.0:2.2:2.2 | 1.8 | 94 |
| A[1] | EDC (35) | 2-N | 1.0:2.1:2.1 | 2.0 | 63 |
| B | EDC (28) | 2-N | 1.0:2.2:2.2 | 2.2 | 11 |
| C | EDC (14) | 2-N | 1.0:2.2:2.2 | 0.8 | 7 |
| D | $CHCl_3$ (20) | 2-N | 1.0:4.0:2.0 | 2.5 | 33 |
| E | EDC(14) | 2-N | 1.0:2.2:2.2 | 1.5 | 20 |
| F | MeOH (16) | 2-N | 1.0:2.2:2.2 | 2.0 | 53 |
| G | MeOH (16) | 2-N | 1.0:2.2:2.2 | 3.3 | 57 |
| H[2] | EDC (13) | 2-N | 1.0:2.2:2.2 | 2.5 | 18 |
| I[3] | MeOH (20) | 2-N | 1.0:2.2:2.2 | 2.6 | 62 |
| J | EDC (21) | 2-N | 1.0:2.8:2.8 | 2.0 | 38 |
| K | EDC (17) | 2-N | 1.0:2.2:2.2 | 0.5 | 8 |
| L | EDC (17) | 2-N | 1.0:2.2:2.2 | 2.0 | 7 |
| M | EDC (35) | 2-N | 1.0:2.4:2.4 | 0.7 | 28 |
| N | EDC (5) | 1-BN | 1.0:1.1:1.1 | 3.4 | 58 |

*Reactant(2-MN, 2-N or 1-BN):HBr:$H_2O_2$
[1]Sulfuric acid was added to the reaction mixture.
[2]Linear alkylbenzene sulfonate was added to the reaction mixture.
[3]Orthophosphoric acid was added to the reaction mixture.

It can be seen from the data on the comparative runs in Table 1 that use of excess HBr/$H_2O_2$, variation of reactant concentration in the solvent, and addition of acids ($H_2SO_4$ and $H_3PO_4$) all failed to increase the conversion of the monobromonaphthol to 1,6-dibromo-2-naphthalene. In contrast, the runs of Examples 1–3 pursuant to this invention achieved 94 to 100% conversions to 1,6-dibromo-2-methoxynaphthalene.

EXAMPLES 4–6

1,6-Dibromo-2-methoxynaphthalene was subjected to hydrodebromination using hydrogen and tungsten carbide as catalyst together with a small amount of ammonium bromide as co-catalyst. In each case the reaction mixture contained 20 wt % of tungsten carbide and the reaction was performed at 115° C. Other conditions and results of these runs are summarized in Table 2, wherein BMN is 2-bromo-6-methoxynaphthalene, DBMN is dibromomethoxynaphthalene, and MN is methoxynaphthalene.

TABLE 2

Hydrodebromination of 1,6-Dibromo-2-Methoxynaphthalene

| Ex. | $NH_4Br$, wt % | Pressure, psi | Time, hrs. | Results, % Normalized |
|---|---|---|---|---|
| 4 | 1 | 95 | 8 | 84% BMN, 8% DBMN, 8% others |
| 5 | 5 | 95 | 6 | 64% BMN, 30% DBMN, 1% MN, 5% others |
| 6 | 1 | 250 | 2.5 | 87% BMN, 3% DBMN, 4% MN, 6% others |

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. In short, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

I claim:

1. A process for the preparation of 1,6-dibromo-2-methoxynaphthalene which comprises generating bromine in situ in a mixture formed by mixing together 2-methoxynaphthalene, hydrogen bromide, at least one peroxidic compound and an organic liquid solvent or diluent under reaction conditions such that bromine is generated in situ and 1,6-dibromo-2-methoxynaphthlene is formed, all of the bromine used in this reaction being in situ generated bromine.

2. A process according to claim 1 wherein water is also used in forming said mixture.

3. A process according to claim 1 wherein the peroxidic compound used in forming the mixture is hydrogen peroxide.

4. A process according to claim 3 wherein the hydrogen peroxide used in forming the mixture is aqueous hydrogen peroxide.

5. A process according to claim 1 wherein the peroxidic compound is added continuously or intermittently portionwise to a mixture formed from 2-methoxynaphthalene, hydrogen bromide, and organic liquid solvent or diluent.

6. A process according to claim 5 wherein the peroxidic compound added to said mixture is hydrogen peroxide.

7. A process according to claim 6 wherein the hydrogen peroxide added to said mixture is an at least 25% aqueous solution of hydrogen peroxide.

8. A process according to claim 1 wherein the peroxidic compound is added continuously or intermittently portionwise to a mixture formed from 2-methoxynaphthalene, hydrogen bromide, water and organic liquid solvent or diluent.

9. A process according to claim 8 wherein the peroxidic compound added to said mixture is hydrogen peroxide.

10. A process according to claim 9 wherein the hydrogen peroxide added to said mixture is an at least 25% aqueous solution of hydrogen peroxide.

11. A process according to any of claims 1 through 10 taken individually wherein the temperature of the mixture in which the bromine is generated in situ is maintained in the range of about 20° to about 90° C.

12. A process for the preparation of 2-bromo-6-methoxynaphthalene which comprises:

a) generating bromine in situ in a mixture formed by mixing together 2-methoxynaphthalene, hydrogen bromide, at least one peroxidic compound and an organic liquid solvent or diluent under reaction conditions such that bromine is generated in situ and 1,6-dibromo-2-methoxynaphthalene is formed, all of the bromine used in this reaction being in situ generated bromine; and b) hydrodebrominating 1,6-dibromo-2-methoxynaphthalene formed in a) to produce 2-bromo-6-methoxynaphthalene.

13. A process according to claim 12 wherein b) is conducted using a carbide-based catalyst.

14. A process according to claim 12 wherein b) is conducted using a catalyst system formed from tungsten carbide and at least one phase transfer catalyst.

15. A process according to claim 12 wherein the peroxidic compound used in forming the mixture of a) is an at least 25% aqueous solution of hydrogen peroxide.

16. A process according to claim 15 wherein water is also used in forming the mixture in a).

17. A process according to any of claims 12 through 16 taken individually wherein the temperature of the mixture of a) in which the bromine is generated in situ is maintained in the range of about 50° to about 70° C.

18. A process for the preparation of 2-bromo-6-methoxynaphthalene which comprises:
   a) generating bromine in situ in a mixture formed by mixing together 2-methoxynaphthalene, hydrogen bromide, at least one peroxidic compound and an organic liquid solvent or diluent under reaction conditions such that 1,6-dibromo-2-methoxynaphthalene is formed; and
   b) hydrodebrominating 1,6-dibromo-2-methoxynaphthalene formed in a) using a catalyst system formed from tungsten carbide and at least one phase transfer catalyst to produce 2-bromo-6-methoxynaphthalene.

19. A process according to claim 18 wherein the peroxidic compound used in forming the mixture of a) is an at least 25% aqueous solution of hydrogen peroxide.

20. A process according to claim 18 wherein water is also used in forming the mixture in a).

21. A process according to claim 18 wherein the temperature of the mixture of a) in which the bromine is generated in situ is maintained in the range of about 50° to about 70° C.

22. A process according to claim 18 wherein the peroxidic compound used in forming the mixture of a) is an at least 25% aqueous solution of hydrogen peroxide, and wherein the temperature of the mixture of a) in which the bromine is generated in situ is maintained in the range of about 50° to about 70° C.

\* \* \* \* \*

UNITED STATES PATENT AND TRADEMARK OFFICE
CERTIFICATE OF CORRECTION

PATENT NO. : 5,840,996
DATED : Nov. 24, 1998
INVENTOR(S) : Mahmood Sabahi

It is certified that error appears in the above-indentified patent and that said Letters Patent is hereby corrected as shown below:

Column 10, Line 59, reads "... using a carbide-based ..." and should read -- ... using a tungsten carbide-based ... --.

Signed and Sealed this

Eleventh Day of May, 1999

*Attest:*

Q. TODD DICKINSON

*Attesting Officer*     *Acting Commissioner of Patents and Trademarks*